(12) United States Patent
Kiris

(10) Patent No.: US 11,751,527 B2
(45) Date of Patent: Sep. 12, 2023

(54) HYBRID SQUASH 'RENEGADE'

(71) Applicant: Enza Zaden Beheer B.V., Enkhuizen (NL)

(72) Inventor: Seyit Kiris, Antalya (TR)

(73) Assignee: Enza Zaden Beheer B.V., Enkhuizen (NL)

( * ) Notice: Subject to any disclaimer, the term of this patent is extended or adjusted under 35 U.S.C. 154(b) by 36 days.

(21) Appl. No.: 17/369,626

(22) Filed: Jul. 7, 2021

(65) Prior Publication Data

US 2023/0016643 A1  Jan. 19, 2023

(51) Int. Cl.
*A01H 1/00*  (2006.01)
*A01H 5/08*  (2018.01)
*A01H 6/34*  (2018.01)

(52) U.S. Cl.
CPC ............. *A01H 6/348* (2018.05); *A01H 1/00* (2013.01); *A01H 5/08* (2013.01)

(58) Field of Classification Search
None
See application file for complete search history.

(56) References Cited

U.S. PATENT DOCUMENTS

| | | |
|---|---|---|
| 5,777,196 A | 7/1998 | Hall |
| 5,948,957 A | 9/1999 | Chapko et al. |
| 5,959,185 A | 9/1999 | Streit et al. |
| 5,969,212 A | 10/1999 | Getschman |
| 5,973,234 A | 10/1999 | Mueller et al. |
| 5,977,445 A | 11/1999 | Soper et al. |
| 2013/0055427 A1* | 2/2013 | Johnson ............. A01H 6/348 800/278 |

OTHER PUBLICATIONS

Berry et al., (2003). "Assessing Probability of Ancestry Using Simple Sequence Repeat Profiles: Applications to Maize Inbred Lines and Soybean Varieties," Genetics, 165:331-342.
Cregan et al., (1999). "An Integrated Genetic Linkage Map of the Soybean Genome," Crop Science, 39:1464-1490.
Enza Zaden USA, Inc. Apr. 2021. 'Renegade F1'. Vegetable Seed Catalogue USA & Canada 2021. Available online at <https://webkiosk.enzazaden.com/vegetable-seed-catalogue-usa-canada-2021/65574518>, p. 46.
Enza Zaden. 'Renegade F1'. Products & Services. Available online at <https://www.enzazaden.com/us/products-and-services/our-products/Squash/Renegade%20F1>, Obtained on Jun. 7, 2021. 1 page.

* cited by examiner

*Primary Examiner* — Phuong T Bui
(74) *Attorney, Agent, or Firm* — Foley Hoag LLP; Brendan T. Jones

(57) ABSTRACT

A seed of hybrid squash designated as 'Renegade' is disclosed. The invention relates to the seeds of hybrid squash 'Renegade', to the plants of hybrid squash 'Renegade', to methods for producing a hybrid plant, and to methods for producing other squash lines, cultivars or hybrids derived from the hybrid squash 'Renegade'.

14 Claims, 4 Drawing Sheets
(4 of 4 Drawing Sheet(s) Filed in Color)

HYBRID SQUASH 'RENEGADE'

FIELD

The present disclosure relates to the field of plant breeding. In particular, this disclosure relates to a new and distinctive squash, *Cucurbita pepo* L., hybrid designated 'Renegade'.

BACKGROUND

Squash (*Cucurbita pepo* L.) is a member of the family Cucurbitaceae. The Cucurbitaceae is a family of about 90 genera and 700 to 760 species, mostly in the tropics. The family includes squashes, melons, pumpkins, gourds, watermelon, loofah, and many weeds. Five species in the genus *Cucurbita*, *Cucurbita argyrosperma*, *C. ficifolia*, *C. maxima*, *C. moschata*, and *C. pepo*, are domesticated. Squash (*Cucurbita pepo* L.) is a morphologically diverse species that includes various subspecies and cultivars. Based on shape, the edible varieties of squash (*Cucurbita pepo* L.) can be divided into eight groups: zucchini (*C. pepo* L. var. cylindrical Paris), vegetable marrow (*C. pepo* L. var. fastigata Paris), pumpkin (*C. pepo* L. var. pepo L. Bailey), scallop (*C. pepo* L. var. clypeata Alefield), acorn (*C. pepo* L. var. turbinate Paris), crookneck (*C. pepo* L. var. torticollia Alefield), straightneck (*C. pepo* L. var. recticollis Pans), and cocozzelle (*C. pepo* L. var. ionga Paris). Squash is usually monoecious, with separate male and female flowers on the same plant. Some squash varieties have vegetative parthenocarpy, thus the plants do not require pollination or other stimulation to produce fruit.

Some cultivars of squash are considered summer squash because the fruits have short storage lives. Summer squashes are harvested when immature, while the rind is still tender and edible. The groups considered summer squash are zucchini, scallop, crookneck, straightneck, and cocozzelle. Zucchini is the most common group of cultivars at present. Its plants are generally semi-shrubby and its cylindrical fruit does not broaden or broadens only slightly. It is eaten as a vegetable in the unripe state. When grown to full maturity, the fruit rind becomes hardened and is often referred to as vegetable marrow. Scallop has a semi-shrubby habit, the fruit ranges from flat to almost discoidal, with undulations or equatorial margins, and it is eaten before maturity. Crookneck is a shrubby type, with yellow, golden or white fruit which is claviform and curved at the distal or apical end and generally has a verrucose rind. It is eaten unripe since the rind and the flesh harden when ripe. Straightneck is a shrubby plant with yellow or golden fruit and a verrucose rind similar to that of var. torticollia. Cocozzelle has cylindrical, long fruit that is slender and slightly bulbous at the apex; it is eaten in the unripe state and one of the most common names is Cocozzelle.

Other cultivars of squash are considered winter squash because the fruits can be stored for several months. Winter squashes are harvested and eaten in the mature stage when the seeds within have fully matured and the skin has hardened into a tough rind. The groups considered winter squash are pumpkin, vegetable marrow, and acorn. Pumpkin includes cultivars of creeping plants which produce spherical, oval or oblate fruit that is rounded or flat at the ends. The fruit of this group is grown to be eaten when ripe and sometimes is used as fodder. Some cultivars of *Cucurbita maxima*, *C. argyrosperma*, and *C. moschata* that produce round, deep yellow or orange colored quash with slightly ribbed rind are also sometimes called "pumpkin". Vegetable marrow has creeper characteristics as a semi-shrub and has short cylindrical fruit that is slightly broader at the apex, with a smooth rind which hardens and thickens on ripening and which varies in color from cream to dark green. Acorn is both a shrubby and creeping plant with fruit which is obovoid or conical, pointed at the apex and longitudinally costate-grooved. The rind is soft, hence the fruit can be eaten in the ripe state.

There is a continued need for new squash varieties. In particular, there is a need for improved squash varieties that are stable, high yielding, and agronomically sound.

BRIEF SUMMARY

In order to meet these needs, the present disclosure is directed to improved hybrid squash varieties.

In one aspect, the present disclosure is directed to a hybrid squash, *Cucurbita pepo* L., seed designated as 'Renegade' having NCIMB Accession Number 43887. In an embodiment of this aspect, the present disclosure is directed to a *Cucurbita pepo* L. squash plant and parts isolated therefrom produced by growing 'Renegade' squash seed. In another embodiment of this aspect, the present disclosure is directed to a *Cucurbita pepo* L. plant and parts isolated therefrom having all the physiological and morphological characteristics of a *Cucurbita pepo* L. plant produced by growing 'Renegade' squash seed having NCIMB Accession Number 43887.

Squash plant parts include squash leaves, ovules, pollen, seeds, squash fruits, parts of squash fruits, flowers, cells, and the like. In another embodiment, the present disclosure is further directed to squash leaves, ovules, pollen, seeds, squash fruits, parts of squash fruits, and/or flowers isolated from 'Renegade' squash plants. In certain embodiments, the present disclosure is further directed to pollen or ovules isolated from 'Renegade' squash plants. In another embodiment, the present disclosure is further directed to protoplasts produced from 'Renegade' squash plants. In another embodiment, the present disclosure is further directed to tissue culture of 'Renegade' squash plants, and to squash plants regenerated from the tissue culture, where the plant has all of the morphological and physiological characteristics of 'Renegade' squash. In certain embodiments, tissue culture of 'Renegade' squash plants is produced from a plant part selected from leaf, anther, pistil, stem, petiole, root, root tip, fruit, seed, flower, cotyledon, hypocotyl, embryo and meristematic cell.

In a further aspect, the present disclosure is directed to a method of producing a seed of a 'Renegade'-derived squash plant, including the steps: (a) crossing a hybrid squash designated as 'Renegade', representative sample of seed having been deposited under NCIMB Accession Number 43887 with itself or a second squash plant; and (b) whereby seed of a 'Renegade'-derived squash plant forms. In another embodiment of this aspect, the method further includes (c) crossing a plant grown from 'Renegade'-derived squash seed with itself or a second squash plant to yield additional 'Renegade'-derived squash seed; (d) growing the additional 'Renegade'-derived squash seed of step (c) to yield additional 'Renegade'-derived squash plants; and (e) repeating the crossing and growing of steps (c) and (d) for an additional 3-10 generations to generate further 'Renegade'-derived squash plants.

In yet another aspect, the present disclosure is directed to a method of vegetatively propagating a plant of hybrid squash variety 'Renegade', the method comprising the steps of: (a) collecting tissue capable of being propagated from a plant of hybrid squash variety 'Renegade', representative seed of said hybrid squash variety having been deposited under NCIMB Accession Number 43887; and (b) producing a rooted plant from said tissue. In another embodiment, the present disclosure is further directed to squash plants, plant parts and seeds produced by the squash plants where the squash plants are produced by any of the preceding methods of the disclosure.

According to the disclosure, there is provided a hybrid squash plant designated 'Renegade'. This disclosure thus relates to the seeds of hybrid squash 'Renegade' and to the plants of squash 'Renegade'. This disclosure also relates to methods for producing other squash cultivars or hybrids derived from hybrid squash 'Renegade' and to the squash cultivars and hybrids derived by the use of those methods.

In another embodiment, the present disclosure is directed to single gene converted plants of hybrid squash 'Renegade'. The single transferred gene may preferably be a dominant or recessive allele. Preferably, the single transferred gene will confer such trait as sex determination, herbicide resistance, insect resistance, resistance for bacterial, fungal, or viral disease, improved harvest characteristics, enhanced nutritional quality, or improved agronomic quality. The single gene may be a naturally occurring squash gene or a transgene introduced through genetic engineering techniques.

In another embodiment, the present disclosure is directed to methods for developing squash plants in a squash plant breeding program using plant breeding techniques including recurrent selection, backcrossing, pedigree breeding, restriction fragment length polymorphism enhanced selection, genetic marker enhanced selection, and transformation. Marker loci such as restriction fragment polymorphisms or random amplified DNA have been published for many years and may be used for selection (See, Pierce et al., *HortScience* (1990) 25:605-615; Wehner, T., *Cucurbit Genetics Cooperative Report*, (1997) 20: 66-88; and Kennard et al., *Theoretical Applied Genetics* (1994) 89:217-224). Seeds, squash plants, and parts thereof produced by such breeding methods are also part of the disclosure.

In additional embodiments, the present disclosure is directed to squash seeds resulting from methods of making a squash variety of the present disclosure. In additional embodiments, the present disclosure is directed to squash plants, and parts thereof, obtained from growing the seeds of the present disclosure. In additional embodiments, the present disclosure is directed to squash plants, and parts thereof, having all the physiological and morphological characteristics of the squash plants of the present disclosure. In additional embodiments, the present disclosure is directed to squash tissue culture, obtained from the plants of the present disclosure. In further embodiments, the tissue culture of the present disclosure is produced from a plant part selected from the group consisting of leaf, anther, pistil, stem, petiole, root, root tip, fruit, seed, flower, cotyledon, hypocotyl, embryo, and meristematic cell.

In addition to the exemplary aspects and embodiments described above, further aspects and embodiments will become apparent by reference by study of the following descriptions.

BRIEF DESCRIPTION OF THE DRAWINGS

The patent or application file contains at least one drawing executed in color. Copies of this patent or patent application publication with color drawings will be provided by the office upon request and payment of the necessary fee.

DETAILED DESCRIPTION

Figure 1:
FIG. 1 shows a plant of hybrid squash 'Renegade'.

There are numerous steps in the development of any novel, desirable plant germplasm. Plant breeding begins with the analysis and definition of problems and weaknesses of the current germplasm, the establishment of program goals, and the definition of specific breeding objectives. The next step is selection of germplasm that possess the traits to meet the program goals. The selected germplasm is crossed in order to recombine the desired traits and through selection varieties or parent lines are developed. The goal is to combine in a single variety or hybrid an improved combination of desirable traits from the parental germplasm. These important traits may include higher yield, field performance, fruit and agronomic quality such as fruit shape and length, resistance to diseases and insects, and tolerance to drought and heat.

Choice of breeding or selection methods can depend on the mode of plant reproduction, the heritability of the trait(s) being improved, and the type of cultivar used commercially (e.g., $F_1$ hybrid cultivar, pureline cultivar, etc.). For highly heritable traits, a choice of superior individual plants evaluated at a single location will be effective, whereas for traits with low heritability, selection should be based on mean values obtained from replicated evaluations of families of related plants. Popular selection methods commonly include pedigree selection, modified pedigree selection, mass selection, and recurrent selection.

The complexity of inheritance influences choice of the breeding method. Backcross breeding is used to transfer one or a few favorable genes for a highly heritable trait into a desirable cultivar. This approach has been used extensively for breeding disease-resistant varieties. Various recurrent selection techniques are used to improve quantitatively inherited traits controlled by numerous genes. The use of recurrent selection in self-pollinating crops depends on the ease of pollination, the frequency of successful hybrids from each pollination, and the number of hybrid offspring from each successful cross.

Each breeding program may include a periodic, objective evaluation of the efficiency of the breeding procedure. Evaluation criteria vary depending on the goal and objectives, and can include gain from selection per year based on comparisons to an appropriate standard, overall value of the advanced breeding lines, and number of successful cultivars produced per unit of input (e.g., per year, per dollar expended, etc.).

Promising advanced breeding lines are thoroughly tested and compared to appropriate standards in environments representative of the commercial target area(s) for at least three years. The best lines can then be candidates for new commercial cultivars. Those still deficient in a few traits may be used as parents to produce new populations for further selection. These processes, which lead to the final step of marketing and distribution, may take from ten to twenty years from the time the first cross or selection is made.

One goal of squash plant breeding is to develop new, unique, and genetically superior squash cultivars and hybrids. A breeder can initially select and cross two or more parental lines, followed by repeated selfing and selection, producing many new genetic combinations. A plant breeder can then select which germplasms to advance to the next generation. These germplasms may then be grown under different geographical, climatic, and soil conditions, and further selections can be made during, and at the end of, the growing season.

The development of commercial squash cultivars thus requires the development of squash parental lines, the crossing of these lines, and the evaluation of the crosses. Pedigree breeding and recurrent selection breeding methods may be used to develop cultivars from breeding populations. Breeding programs can be used to combine desirable traits from two or more varieties or various broad-based sources into breeding pools from which lines are developed by selfing and selection of desired phenotypes. The new lines are crossed with other lines and the hybrids from these crosses are evaluated to determine which have commercial potential.

Pedigree breeding is generally used for the improvement of self-pollinating crops or inbred lines of cross-pollinating crops. Two parents which possess favorable, complementary traits are crossed to produce an $F_1$. An $F_2$ population is produced by selfing one or several $F_1$s or by intercrossing two $F_1$s (sib mating). Selection of the best individuals is usually begun in the $F_2$ population; then, beginning in the $F_3$, the best individuals in the best families are selected. Replicated testing of families, or hybrid combinations involving individuals of these families, often follows in the $F_4$ generation to improve the effectiveness of selection for traits with low heritability. At an advanced stage of inbreeding (i.e., $F_6$ and $F_7$), the best lines or mixtures of phenotypically similar lines are tested for potential release as new varieties.

Mass and recurrent selections can be used to improve populations of either self- or cross-pollinating crops. A genetically variable population of heterozygous individuals is either identified or created by intercrossing several different parents. The best plants are selected based on individual superiority, outstanding progeny, or excellent combining ability. The selected plants are intercrossed to produce a new population in which further cycles of selection are continued.

Backcross breeding may be been used to transfer genes for a simply inherited, highly heritable trait into a desirable homozygous cultivar or line that is the recurrent parent. The source of the trait to be transferred is called the donor parent. The resulting plant is expected to have the attributes of the recurrent parent (e.g., cultivar) and the desirable trait transferred from the donor parent. After the initial cross, individuals possessing the phenotype of the donor parent are selected and repeatedly crossed (backcrossed) to the recurrent parent. The resulting plant is expected to have the attributes of the recurrent parent (e.g., cultivar) and the desirable trait transferred from the donor parent.

The single-seed descent procedure in the strict sense refers to planting a segregating population, harvesting a sample of one seed per plant, and using the one-seed sample to plant the next generation. When the population has been advanced from the $F_2$ to the desired level of inbreeding, the plants from which lines are derived will each trace to different $F_2$ individuals. The number of plants in a population declines each generation due to failure of some seeds to germinate or some plants to produce at least one seed. As a result, not all of the $F_2$ plants originally sampled in the population will be represented by a progeny when generation advance is completed.

In addition to phenotypic observations, the genotype of a plant can also be examined. There are many laboratory-based techniques known in the art that are available for the analysis, comparison and characterization of plant genotype. Such techniques include, without limitation, Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLPs), Simple Sequence Repeats (SSRs—which are also referred to as Microsatellites), and Single Nucleotide Polymorphisms (SNPs).

Molecular markers can also be used during the breeding process for the selection of qualitative traits. For example, markers closely linked to alleles or markers containing sequences within the actual alleles of interest can be used to select plants that contain the alleles of interest during a backcrossing breeding program. The markers can also be used to select toward the genome of the recurrent parent and against the markers of the donor parent. This procedure attempts to minimize the amount of genome from the donor parent that remains in the selected plants. It can also be used to reduce the number of crosses back to the recurrent parent needed in a backcrossing program. The use of molecular markers in the selection process is often called genetic marker enhanced selection or marker-assisted selection. Molecular markers may also be used to identify and exclude certain sources of germplasm as parental varieties or ancestors of a plant by providing a means of tracking genetic profiles through crosses.

Mutation breeding may also be used to introduce new traits into squash varieties. Mutations that occur spontaneously or are artificially induced can be useful sources of variability for a plant breeder. The goal of artificial mutagenesis is to increase the rate of mutation for a desired characteristic. Mutation rates can be increased by many different means including temperature, long-term seed storage, tissue culture conditions, radiation (such as X-rays, Gamma rays, neutrons, Beta radiation, or ultraviolet radiation), chemical mutagens (such as base analogs like 5-bromo-uracil), antibiotics, alkylating agents (such as sulfur mustards, nitrogen mustards, epoxides, ethyleneamines, sulfates, sulfonates, sulfones, or lactones), azide, hydroxylamine, nitrous acid or acridines. Once a desired trait is observed through mutagenesis the trait may then be incorporated into existing germplasm by traditional breeding techniques. Details of mutation breeding can be found in *Principles of Cultivar Development* by Fehr, Macmillan Publishing Company, 1993.

The production of double haploids can also be used for the development of homozygous varieties in a breeding program. Double haploids are produced by the doubling of a set of chromosomes from a heterozygous plant to produce a completely homozygous individual. For example, see Wan et al., *Theor. Appl. Genet.*, 77:889-892, 1989.

Additional non-limiting examples of breeding methods that may be used include, without limitation, those found in *Principles of Plant Breeding*, John Wiley and Son, pp. 115-161, 1960; Allard, 1960; Simmonds, 1979; Sneep et al., 1979; Fehr, 1987; "Carrots and Related Vegetable Umbelliferae", Rubatzky, V. E., et al., 1999.

Definitions

In the description that follows, a number of terms are used. In order to provide a clear and consistent understanding of the specification and claims, including the scope to be given such terms, the following definitions are provided:

Allele. The allele is any of one or more alternative forms of a gene, all of which relate to one trait or characteristic. In a diploid cell or organism, the two alleles of a given gene occupy corresponding loci on a pair of homologous chromosomes.

Backcrossing. Backcrossing is a process in which a breeder repeatedly crosses hybrid progeny back to one of the parents, for example, a first generation hybrid $F_1$ with one of the parental genotype of the $F_1$ hybrid.

Essentially all the physiological and morphological characteristics. A plant having essentially all the physiological and morphological characteristics means a plant having the physiological and morphological characteristics of the recurrent parent, except for the characteristics derived from the converted gene.

Gene. As used herein, "gene" refers to a segment of nucleic acid. A gene can be introduced into a genome of a species, whether from a different species or from the same species, using transformation or various breeding methods.

Intermediate resistant or Intermediate resistance. Intermediate resistant refers to plant varieties that restrict the growth and development of the specified pest or pathogen, but may exhibit a greater range of symptoms or damage compared to highly resistant varieties. Intermediate resistant plant varieties will still show less severe symptoms or damage than susceptible plant varieties when grown under similar environmental conditions and/or pest or pathogen pressure.

Parthenocarpic. "Parthenocarpic" refers to the ability of fruit to develop without pollination or fertilization. The fruit are therefore seedless when not pollinated, but can produce seeds if pollinated.

Propagate. To "propagate" a plant means to reproduce the plant by means including, but not limited to, seeds, cuttings, divisions, tissue culture, embryo culture or other in vitro method.

Quantitative Trait Loci (QTL). Quantitative trait loci refer to genetic loci that control to some degree numerically representable traits that are usually continuously distributed.

Regeneration. Regeneration refers to the development of a plant from tissue culture.

Single gene converted. Single gene converted or conversion plant refers to plants which are developed by a plant breeding technique called backcrossing wherein essentially all of the desired morphological and physiological characteristics of an inbred are recovered in addition to the single gene transferred into the inbred via the backcrossing technique, genetic engineering or mutation.

Vegetative propagation. Refers to taking part of a plant and allowing that plant part to form roots where plant part is defined as leaf, pollen, embryo, cotyledon, hypocotyl, meristematic cell, root, root tip, pistil, anther, flower, shoot tip, shoot, stem, fruit and petiole.

Overview of the Hybrid 'Renegade'

Figure 2:
FIG. 2 shows fruit attached to a plant of hybrid squash 'Renegade'.
Figure 3:
FIG. 3 shows detached fruit of hybrid squash 'Renegade'.
Figure 4:
FIG. 4 shows a leaf, flowers, and fruit of hybrid squash 'Renegade'.

Hybrid squash 'Renegade' is a zucchini type squash that has a bush growth habit, a medium area of silvery patches on leaf blade, and produces fruit that has a dark green skin color at market stage. Hybrid squash 'Renegade' is suitable for open field cultivation on the east coast of North America. Hybrid squash cultivar 'Renegade' is highly resistant to Zucchini yellow mosaic virus (ZYMV), Watermelon mosaic virus (WMV), and Papaya ringspot virus (PRSV) and intermediate resistant to powdery mildew (*Podosphaera xanthii*, Px). FIG. 1 depicts a plant of hybrid squash 'Renegade'. FIG. 2 depicts fruit attached to a plant of hybrid squash 'Renegade'. FIG. 3 depicts detached fruit of hybrid squash 'Renegade'. FIG. 4 depicts a leaf, flowers, and fruit of hybrid squash 'Renegade'.

Hybrid squash 'Renegade' has shown uniformity and stability for the traits, within the limits of environmental influence for the traits. Hybrid squash 'Renegade' has been increased with continued observation for uniformity. No variant traits have been observed or are expected in 'Renegade'.

Objective Description of the Hybrid 'Renegade'

The information presented in this section was determined in trial experiments in accordance with official Dutch plant variety registration authorities (Naktuinbouw). The terminology and descriptors used by the Naktuinbouw, and accordingly in this section, are in line with the descriptors of the "UPOV Guidelines for the Conduct of Tests for Distinctness, Uniformity, and Stability", or the "Test Guidelines" for *Cucurbita pepo* L. The "Test Guidelines" indicate reference varieties for the descriptors or characteristics that are included in the list. The terminology and descriptors used in these tables are in line with the official terminology as of the filing date, and are thus clear for a person skilled in the art.

Hybrid squash 'Renegade' has the following morphologic and other characteristics:

Fruit type: Zucchini
Plant:
Growth habit: Bush
Parthenocarpy: Absent
Branching: Absent
Attitude of petiole (excluding lower external leaves): Erect
Stem:
Color: RHS 136A (Dark green)
Stem mottling: Absent
Development of tendrils: Few
Leaf blade:
Length: 26 cm
Width: 34 cm
Color: RHS N134 Å (Dark yellowish green)
Blistering: Absent
Pubescence on dorsal surface: Absent
Pubescence on ventral surface: Sparse
Petiole length: 35 cm
Incisions: Deep
Silvery patches: Medium strong
Relative area covered by silvery patches: Medium
Petiole:
Length: 35 cm (medium)
Spines: Few
Flower:
Female flower diameter: 14 cm
Female flower color: RHS 17A (Strong orange yellow)
Leaf cacila female flower: RHS 142A (Strong yellow green)
Male flower diameter: 12 cm
Male flower color: RHS 23A (Vivid orange yellow)
Leaf cacila male flower: RHS 141C (Strong yellowish green)
Young fruit:
Main color of skin (excluding color of ribs or grooves): RHS 141B (Deep
yellowish green)
Fruit at market maturity:
General shape: Cylindrical
Main color of skin (excluding color of dots, patches, stripes and bands): RHS 135A (Dark green)
Intensity of main color: Dark
Dots: Present
Size of main dots: Small to medium
Glossiness: High
Maturity: Intermediate
Length: 21 cm
Width: 4.5 cm
Weight: 238 g
Grooves: Absent
Ribs: Absent
Size of flower scar: 10 mm
Blossom end shape: Star shape
Peduncle length: 3 cm
Peduncle color: RHS 143B (Strong yellow green)
Mottling of peduncle: Present
Ripe fruit:
Main color of skin (excluding color of mottles, patched, stripes and bands): Yellow
Seed:
Length: 14-15 mm
Width: 8 mm
Disease and pest resistances:
Zucchini yellow mosaic virus (ZYMV): Highly resistant
Watermelon mosaic virus (WMV): Highly resistant
Papaya ringspot virus (PRSV): Highly resistant
Powdery mildew (*Podosphaera xanthii*, Px): Intermediate resistant
Comparisons to Other Squash Variety Table 1 below compares characteristics of hybrid squash 'Renegade' with the squash variety 'Keesha' (unpatented). Column 1 lists the characteristics, column 2 shows the characteristics for hybrid squash 'Renegade', and column 3 shows the characteristics for squash variety 'Keesha'.

TABLE 1

| Characteristic | 'Renegade' | 'Keesha' |
|---|---|---|
| Leaf cacila male flower | RHS 141C (Strong yellowish green) | Yellow or green |
| Leaf cacila female flower | RHS 142A (Strong yellow green) | Yellow |
| Size of dots (second color of skin) | Small and medium dots | Small dots |
| Leaf silvering | Medium strong | Absent |

Further Embodiments

This disclosure also is directed to methods for producing a squash plant by crossing a first parent squash plant with a second parent squash plant wherein either the first or second parent squash plant is a hybrid squash plant of 'Renegade'. Further, both first and second parent squash plants can come from the hybrid squash 'Renegade'. All plants produced using hybrid squash 'Renegade' as a parent are within the scope of this disclosure, including plants derived from hybrid squash 'Renegade'. Plants derived from hybrid squash 'Renegade' may be used, in certain embodiments, for the development of new squash varieties. By selecting plants having one or more desirable traits, a plant derived from hybrid squash 'Renegade' is obtained which possesses some of the desirable traits of the hybrid as well as potentially other selected traits.

The development of new varieties using one or more starting varieties is well known in the art. In accordance with this disclosure, novel varieties may be created by crossing hybrid squash 'Renegade' followed by multiple generations of breeding according to such well known methods. New varieties may be created by crossing with any second plant. In selecting such a second plant to cross for the purpose of developing novel lines, it may be desired to choose those plants which either themselves exhibit one or more selected desirable characteristics or which exhibit the desired characteristic(s) when in hybrid combination. Once initial crosses have been made, inbreeding and selection take place to produce new varieties. For development of a uniform line, often five or more generations of selfing and selection are involved.

It is preferred to breed for a combination of desirable plant characteristics and resistances to create a single variety or hybrid containing an improved combination of desirable traits from the parental germplasm. The development of commercial squash hybrids relates to the development of squash parental lines, the crossing of these lines, and the evaluation of the crosses. Hybrid varieties offer multiple advantages, including a combination of desirable dominant and recessive traits from a set of inbred parents. Pedigree breeding and recurrent selection breeding methods are used to develop cultivars from breeding populations. Breeding programs combine desirable traits from two or more varieties or various broad-based sources into breeding pools from which lines are developed by selfing and selection of desired phenotypes. The new lines are crossed with other lines and the hybrids from these crosses are evaluated to determine which have the desirable characteristics.

As used herein, the term plant includes plant cells, plant protoplasts, plant cell tissue cultures from which squash plants can be regenerated, plant calli, plant clumps and plant cells that are intact in plants or parts of plants, such as embryos, pollen, ovules, flowers, leaves, stems, and the like.
Genetic Marker Profile Through SSR and First Generation Progeny In addition to phenotypic observations, a plant can also be identified by its genotype. The genotype of a plant can be characterized through a genetic marker profile, which can identify plants of the same variety or a related variety or be used to determine or validate a pedigree. Genetic marker profiles can be obtained by techniques such as Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLPs), Simple Sequence Repeats (SSRs) which are also referred to as Microsatellites, and Single Nucleotide Polymorphisms (SNPs). For example, see Cregan et al., "An Integrated Genetic Linkage Map of the Soybean Genome" Crop Science 39:1464-1490 (1999), and Berry et al., "Assessing Probability of Ancestry Using Simple Sequence Repeat Profiles: Applications to Maize Inbred Lines and Soybean Varieties" Genetics 165:331-342 (2003).

Particular markers used for these purposes are not limited to any particular set of markers, but are envisioned to include any type of marker and marker profile, which provides a means of distinguishing varieties.

The present disclosure includes a hybrid squash plant characterized by molecular and physiological data obtained from the representative sample of said variety deposited with the National Collection of Industrial, Food and Marine Bacteria Ltd. (NCIMB Ltd.).

Means of performing genetic marker profiles using SSR polymorphisms are well known in the art. SSRs are genetic markers based on polymorphisms in repeated nucleotide sequences, such as microsatellites. A marker system based on SSRs can be highly informative in linkage analysis relative to other marker systems in that multiple alleles may be present. Another advantage of this type of marker is that, through use of flanking primers, detection of SSRs can be achieved, for example, by polymerase chain reaction (PCR), thereby eliminating the need for labor-intensive Southern hybridization. PCR detection is done by use of two oligonucleotide primers flanking the polymorphic segment of repetitive DNA. Repeated cycles of heat denaturation of the DNA followed by annealing of the primers to their complementary sequences at low temperatures, and extension of the annealed primers with DNA polymerase, include the major part of the methodology.

Following amplification, markers can be scored by electrophoresis of the amplification products. Scoring of marker genotype is based on the size of the amplified fragment, which may be measured by the number of base pairs of the fragment. While variation in the primer used or in laboratory procedures can affect the reported fragment size, relative values should remain constant regardless of the specific primer or laboratory used. When comparing varieties it is preferable if all SSR profiles are performed in the same lab.

Single-Gene Conversions

When the terms squash plant, cultivar, hybrid or squash line are used in the context of the present disclosure, this also includes any single gene conversions of that line. The term "single gene converted plant" as used herein refers to those squash plants which are developed by a plant breeding technique called backcrossing wherein essentially all of the desired morphological and physiological characteristics of a cultivar are recovered in addition to the single gene transferred into the line via the backcrossing technique. Backcrossing methods can be used with the present disclosure to improve or introduce a characteristic into the line. The term "backcrossing" as used herein refers to the repeated crossing of a hybrid progeny back to one of the parental squash plants for that line, backcrossing 1, 2, 3, 4, 5, 6, 7, 8 or more times to the recurrent parent. The parental squash plant which contributes the gene for the desired characteristic is termed the nonrecurrent or donor parent. This terminology refers to the fact that the nonrecurrent parent is used one time in the backcross protocol and therefore does not recur. The parental squash plant to which the gene or genes from the nonrecurrent parent are transferred is known as the recurrent parent as it is used for several rounds in the backcrossing protocol (Poehlman & Sleper, 1994; Fehr, 1987). In a typical backcross protocol, the original cultivar of interest (recurrent parent) is crossed to a second line (nonrecurrent parent) that carries the single gene of interest to be transferred. The resulting progeny from this cross are then crossed again to the recurrent parent and the process is repeated until a squash plant is obtained wherein essentially all of the desired morphological and physiological characteristics of the recurrent parent are recovered in the converted plant, in addition to the single transferred gene from the nonrecurrent parent.

The selection of a suitable recurrent parent is an important step for a successful backcrossing procedure. The goal of a backcross protocol is to alter or substitute a single trait or characteristic in the original line. To accomplish this, a single gene of the recurrent cultivar is modified or substituted with the desired gene from the nonrecurrent parent, while retaining essentially all of the rest of the desired genetic, and therefore the desired physiological and morphological, constitution of the original line. The choice of the particular nonrecurrent parent will depend on the purpose of the backcross, one of the major purposes is to add some commercially desirable, agronomically important trait to the plant. The exact backcrossing protocol will depend on the characteristic or trait being altered to determine an appropriate testing protocol. Although backcrossing methods are simplified when the characteristic being transferred is a dominant allele, a recessive allele may also be transferred. In this instance it may be necessary to introduce a test of the progeny to determine if the desired characteristic has been successfully transferred.

Many single gene traits have been identified that are not regularly selected for in the development of a new line but that can be improved by backcrossing techniques. Single gene traits may or may not be transgenic, examples of these traits include but are not limited to, male sterility, modified fatty acid metabolism, modified carbohydrate metabolism, herbicide resistance, resistance for bacterial, fungal, or viral disease, insect resistance, enhanced nutritional quality, industrial usage, yield stability and yield enhancement. These genes are generally inherited through the nucleus. Several of these single gene traits are described in U.S. Pat. Nos. 5,777,196, 5,948,957 and 5,969,212.

Tissue Culture

Further reproduction of the variety can occur by tissue culture and regeneration. Tissue culture of various tissues of squash and regeneration of plants therefrom is well known and widely published. For example, reference may be had to Teng et al., HortScience. 1992, 27: 9, 1030-1032 Teng et al., HortScience. 1993, 28: 6, 669-1671, Zhang et al., Journal of Genetics and Breeding. 1992, 46: 3, 287-290, Webb et al., Plant Cell Tissue and Organ Culture. 1994, 38: 1, 77-79, Curtis et al., Journal of Experimental Botany. 1994, 45: 279, 1441-1449, Nagata et al., Journal for the American Society for Horticultural Science. 2000, 125: 6, 669-672, and Ibrahim et al., Plant Cell, Tissue and Organ Culture. (1992), 28(2): 139-145. It is clear from the literature that the state of the art is such that these methods of obtaining plants are routinely used and have a very high rate of success. Thus, another aspect of this disclosure is to provide cells which upon growth and differentiation produce squash plants having the physiological and morphological characteristics of hybrid squash 'Renegade'.

As used herein, the term "tissue culture" indicates a composition comprising isolated cells of the same or a different type or a collection of such cells organized into parts of a plant. Exemplary types of tissue cultures are protoplasts, calli, meristematic cells, and plant cells that can generate tissue culture that are intact in plants or parts of plants, such as leaves, pollen, embryos, roots, root tips, anthers, pistils, flowers, seeds, petioles, and the like. Means for preparing and maintaining plant tissue culture are well known in the art. By way of example, a tissue culture comprising organs has been used to produce regenerated plants. U.S. Pat. Nos. 5,959,185; 5,973,234 and 5,977,445 describe certain techniques.

Tissue culture of squash can be used for the in vitro regeneration of squash plants. Tissues cultures of various tissues of squash and regeneration of plants therefrom are well-known and published. By way of example, tissue cultures, some comprising organs to be used to produce regenerated plants, have been described in Burza et al., Plant Breeding. 1995, 114: 4, 341-345, Cui Hongwen et al., Report Cucurbit Genetics Cooperative. 1999, 22, 5-7, Pellinen, Angewandte Botanik. 1997, 71: 3/4, 116-118, Kuijpers et al., Plant Cell Tissue and Organ Culture. 1996, 46: 1, 81-83, Colijn-Hooymans et al., Plant Cell Tissue and Organ Culture. 1994, 39: 3, 211-217, Lou et al., Hort- Science. 1994, 29: 8, 906-909, Tabei et al., Breeding Science. 1994, 44: 1, 47-51, Sarmanto et al., Plant Cell Tissue and Organ Culture 31:3 185-193 (1992), Raharjo et al., Reports Cucurbits Genetics Cooperative 15, 35-39 (1992), Garcia-Sobo et al., Reports Cucurbits Genetics Cooperative 15, 40-44 (1992), Cade et al., Journal of the American Society for Horticultural Science 115:4 691-696 (1990), Chee et al., HortScience 25:7, 792-793 (1990), Kim et al., HortScience 24:4 702 (1989), and Punja et al., Plant Cell Report 9:2 61-64 (1990). It should also be mentioned that the regeneration of the squash after induction of adventitious shoot buds on calli derived from cotyledons has been described in Msikita et al., Cucurbit Genetics Cooperative Reports, 11: 5-7 (1988) and Kim et al., Plant Cell Tissue Organ Culture, 12: 67-74 (1988). Wehner et al., HortScience 16: 759-760 (1981) had previously described the induction of buds on cotyledons. Squash plants may be regenerated by somatic embryogenesis. These somatic embryos developed either in cell suspensions derived from calli developed from leaf explants (Chee et al., Plant Cell Report 7: 274-277 (1988)) or hypocotyls (Rajasekaran et al., Annals of Botany, 52: p. 417-420 (1983)) or directly on cotyledons (Cade et al., Cucurbit Genetics Cooperative Reports 11:3-4 (1988)) or leaf calli (Malepszy et al., Pflanzenphysiologie, 111: 273-276 (1983)). It is clear from the literature that the state of the art is such that these methods of obtaining plants are "conventional" in the sense that they are routinely used and have a very high rate of success. Thus, another aspect of this disclosure is to provide cells which upon growth and differentiation produce squash plants having the physiological and morphological characteristics of hybrid squash 'Renegade'.

Additional Breeding Methods

The cultivar of the disclosure can also be used for transformation where exogenous genes are introduced and expressed by the cultivar of the disclosure. Genetic variants of 'Renegade' created either through traditional breeding methods or through transformation of hybrid squash 'Renegade' by any of a number of protocols known to those of skill in the art are intended to be within the scope of this disclosure.

Mutations for use in mutation breeding can be induced in plants by using mutagenic chemicals such as ethyl methane sulfonate (EMS), by irradiation of plant material with gamma rays or fast neutrons, or by other means. The resulting nucleotide changes are random, but in a large collection of mutagenized plants the mutations in a gene of interest can be readily identified by using the TILLING (Targeting Induced Local Lesions IN Genomes) method (McCallum et al. (2000) Targeted screening for induced mutations. Nat. Biotechnol. 18, 455-457, and Henikoff et al. (2004) TILLING. Traditional mutagenesis meets functional genomics. Plant Physiol. 135, 630-636). The principle of this method is based on the PCR amplification of the gene of interest from genomic DNA of a large collection of mutagenized plants in the M2 generation. By DNA sequencing or by looking for point mutations using a single-strand specific nuclease, such as the CEL-I nuclease (Till et al. (2004) Mismatch cleavage by single-strand specific nucleases. Nucleic Acids Res. 32, 2632-2641), the individual plants that have a mutation in the gene of interest are identified. By screening many plants, a large collection of mutant alleles is obtained, each giving a different effect on gene expression or enzyme activity. The gene expression or protein levels can for example be tested by transcript analysis levels (e.g., by RT-PCR) or by quantification of protein levels with antibodies. Plants with the desired reduced gene expression or reduced protein expression are then backcrossed or crossed to other breeding lines to transfer only the desired new allele into the background of the crop wanted.

Genes of interest for use in breeding may also be edited using gene editing techniques including transcription activator-like effector nuclease (TALEN) gene editing techniques, clustered Regularly Interspaced Short Palindromic Repeat (CRISPR/Cas9) gene editing techniques, and/or zinc-finger nuclease (ZFN) gene editing techniques. For this, transgenic plants are generated expressing one or more constructs targeting the gene of interest. These constructs may include, without limitation, an anti-sense construct, an optimized small-RNA construct, an inverted repeat construct, a targeting construct, a guide RNA construct, a construct encoding a targeting protein, and/or a combined sense-anti-sense construct, and may work in conjunction with a nuclease, an endonuclease, and/or an enzyme, so as to downregulate the expression of a gene of interest.

One of ordinary skill in the art of plant breeding would know how to evaluate the traits of two plant varieties to determine if there is no significant difference between the two traits expressed by those varieties. For example, see Fehr and Walt, Principles of Cultivar Development, p. 261-286 (1987). Thus the disclosure includes hybrid squash 'Renegade' progeny squash plants comprising a combination of at least two 'Renegade' traits selected from the group consisting of those listed in Table 1 or the 'Renegade' combination of traits listed in the Summary of the Disclosure, so that said progeny squash plant is not significantly different for said traits than squash 'Renegade' as determined at the 5% significance level when grown in the same environmental conditions and/or may be characterized by percent similarity or identity to hybrid squash 'Renegade' as determined by SSR markers. Using techniques described herein, molecular markers may be used to identify said progeny plant as a hybrid squash 'Renegade' progeny plant. Mean trait values may be used to determine whether trait differences are significant, and preferably the traits are measured on plants grown under the same environmental conditions. Once such a variety is developed its value is substantial since it is important to advance the germplasm base as a whole in order to maintain or improve traits such as yield, disease resistance, pest resistance, and plant performance in extreme environmental conditions.

As used herein, the term "plant" includes plant cells, plant protoplasts, plant cell tissue cultures from which squash plants can be regenerated, plant calli, plant clumps and plant cells that are intact in plants or parts of plants, such as leaves, pollen, embryos, cotyledons, hypocotyl, roots, root tips, anthers, pistils, flowers, seeds, stems and the like.

The use of the terms "a," "an," and "the," and similar referents in the context of describing the disclosure (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. For example, if the range 10-15 is disclosed, then 11, 12, 13, and 14 are also disclosed. All methods described herein can be performed in any suitable order unless otherwise indicated herein or otherwise clearly contradicted by context. The use of any and all examples, or exemplary language (e.g., "such as") provided herein, is intended merely to better illuminate the disclosure and does not pose a limitation on the scope of the disclosure unless otherwise claimed. No language in the specification should be construed as indicating any non-claimed element as essential to the practice of the disclosure.

While a number of exemplary aspects and embodiments have been discussed above, those of skill in the art will recognize certain modifications, permutations, additions, and sub-combinations thereof. It is therefore intended that the following appended claims and claims hereafter introduced are interpreted to include all such modifications, permutations, additions, and sub-combinations as are within their true spirit and scope.

DEPOSIT INFORMATION

A deposit of the hybrid squash 'Renegade' is maintained by Enza Zaden USA, Inc., having an address at 7 Harris Place, Salinas, Calif. 93901, United States. Access to this deposit will be available during the pendency of this application to persons determined by the Commissioner of Patents and Trademarks to be entitled thereto under 37 C.F.R. § 1.14 and 35 U.S.C. § 122. Upon allowance of any claims in this application, all restrictions on the availability to the public of the variety will be irrevocably removed by affording access to a deposit of at least 625 seeds of the same variety with the National Collection of Industrial, Food and Marine Bacteria Ltd. (NCIMB Ltd), Ferguson Building, Craibstone Estate, Bucksburn, Aberdeen, AB21 9YA, United Kingdom.

At least 625 seeds of hybrid squash 'Renegade' were deposited on Nov. 3, 2021 according to the Budapest Treaty in the National Collection of Industrial, Food and Marine Bacteria Ltd (NCIMB Ltd), Ferguson Building, Craibstone Estate, Bucksburn, Aberdeen, AB21 9YA, United Kingdom. The deposit has been assigned NCIMB number 43887. Access to this deposit will be available during the pendency of this application to persons determined by the Commissioner of Patents and Trademarks to be entitled thereto under 37 C.F.R. § 1.14 and 35 U.S.C. § 122. Upon allowance of any claims in this application, all restrictions on the availability to the public of the variety will be irrevocably removed.

The deposit will be maintained in the NCIMB depository, which is a public depository, for a period of at least 30 years, or at least 5 years after the most recent request for a sample of the deposit, or for the effective life of the patent, whichever is longer, and will be replaced if a deposit becomes nonviable during that period.

The invention claimed is:
1. A seed of hybrid squash designated as 'Renegade', representative sample of seed having been deposited under NCIMB Accession Number 43887.
2. A squash plant produced by growing the seed of claim 1.
3. A plant part from the plant of claim 2, wherein said part is a leaf, an ovule, a pollen grain, or a fruit.
4. The plant part of claim 3, wherein said part is a fruit.
5. A squash plant having all the physiological and morphological characteristics of the squash plant of claim 2.
6. A plant part from the plant of claim 5, wherein said part is a leaf, an ovule, a pollen grain, or a fruit.
7. The plant part of claim 6, wherein said part is a fruit.
8. A pollen grain or an ovule of the plant of claim 2.
9. A protoplast produced from the plant of claim 2.
10. A tissue culture of the plant of claim 2, wherein said tissue culture is produced from a plant part selected from the group consisting of leaf, anther, pistil, stem, petiole, root, root tip, fruit, flower, cotyledon, hypocotyl, and meristematic cell.
11. A squash plant regenerated from the tissue culture of claim 10, wherein the plant has all of the morphological and physiological characteristics of a squash plant produced by growing hybrid squash seed designated as 'Renegade', representative sample of seed having been deposited under NCIMB Accession Number 43887.
12. A method of producing a seed of a 'Renegade'-derived squash plant, comprising the step:
 a) crossing a hybrid squash designated as 'Renegade', representative sample of seed having been deposited under NCIMB Accession Number 43887, with itself or a second squash plant, whereby seed of a 'Renegade'-derived squash plant forms.
13. The method of claim 12, further comprising the steps:
 b) crossing a plant grown from 'Renegade'-derived squash seed with itself or a second squash plant to yield additional 'Renegade'-derived squash seed;
 c) growing the additional 'Renegade'-derived squash seed of step (b) to yield additional 'Renegade'-derived squash plants; and
 d) repeating the crossing and growing of steps (b) and (c) for an additional 3-10 generations to generate further 'Renegade'-derived squash plants.
14. A method of vegetatively propagating a plant of hybrid squash variety 'Renegade', the method comprising the steps of:
 (a) collecting tissue capable of being propagated from a plant of hybrid squash variety 'Renegade', representative seed of said hybrid squash variety having been deposited under NCIMB Accession Number 43887; and
 (b) producing a rooted plant from said tissue.

* * * * *